(12) United States Patent
Fukuda et al.

(10) Patent No.: US 7,256,304 B2
(45) Date of Patent: Aug. 14, 2007

(54) PROCESS FOR PRODUCING 3-UNSUBSTITUTED 5-AMINO-4-NITROSOPYRAZOLE COMPOUND, AND 2-HYDROXYIMINO-3-OXOPROPIONITRILE, 3-HYDRAZONO-2-HYDROXYIMINO PROPIONITRILE COMPOUND, AND PROCESSES FOR PRODUCING THESE

(75) Inventors: Yasuhisa Fukuda, Ube (JP); Shoji Shikita, Ube (JP); Tadashi Murakami, Ube (JP); Masayoshi Oku, Ube (JP); Hiroyuki Ota, Ube (JP); Masanori Sone, Ube (JP)

(73) Assignee: UBE Industries, Ltd., Ube-shi (JP)

( * ) Notice: Subject to any disclaimer, the term of this patent is extended or adjusted under 35 U.S.C. 154(b) by 543 days.

(21) Appl. No.: 10/500,599

(22) PCT Filed: Jan. 24, 2003

(86) PCT No.: PCT/JP03/00647

§ 371 (c)(1),
(2), (4) Date: Jul. 1, 2004

(87) PCT Pub. No.: WO03/062207

PCT Pub. Date: Jul. 31, 2003

(65) Prior Publication Data

US 2005/0096472 A1    May 5, 2005

(30) Foreign Application Priority Data

Jan. 24, 2002 (JP) ............................. 2002-015191
Apr. 3, 2002 (JP) ............................. 2002-101259
Apr. 9, 2002 (JP) ............................. 2002-106657
Jul. 5, 2002 (JP) ............................. 2002-197135

(51) Int. Cl.
    C07C 255/17    (2006.01)
    C07D 293/00    (2006.01)

(52) U.S. Cl. ......................... 558/440; 548/100
(58) Field of Classification Search ............... 558/440
    See application file for complete search history.

(56) References Cited

U.S. PATENT DOCUMENTS 3,957,782 A    5/1976    Hoehn 4,665,186 A *    5/1987    Steiner et al. .............. 546/250

FOREIGN PATENT DOCUMENTS

| JP | 60-56981 A | 4/1985 |
| JP | 61-282376 A | 12/1986 |
| JP | 62-273979 A | 11/1987 |
| JP | 1-190668 A | 7/1989 |
| WO | 02/100821 A1 | 12/2002 |

OTHER PUBLICATIONS

Andtianov, V.G. et al., Rearrangements of 1-oxa-2-azoles. 5. Synthesis of α-hydroximinodimethylhydrazones of 1,2,4-oxadiazolyl-3-glyoxal and their rearrangement, Khimiya Geterotsiklicheskikh Soedinenii, (1991), vol. 7, pp. 976-978. Accession No. 1992:128796, CA Abstract No.: 116:128796.

* cited by examiner

*Primary Examiner*—Kamal A. Saeed
(74) *Attorney, Agent, or Firm*—Birch, Stewart, Kolasch & Birch, LLP

(57) ABSTRACT

The present invention is to provide a process for preparing a 3-unsubstituted-5-amino-4-nitrosopyrazole compound represented by the formula (1):

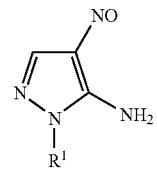

(1)

wherein $R^1$ represents a hydrogen atom, an alkyl group, an aryl group or a heterocyclic group each of which may have a substituent(s), which comprises cyclizing a 3-hydrazono-2-hydroxyiminopropionitrile compound represented by the formula (2):

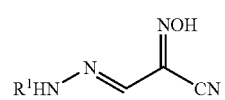

(2)

wherein $R^1$ has the same meaning as defined above, synthetic intermediates thereof and a process for preparing these intermediates.

2 Claims, No Drawings

PROCESS FOR PRODUCING 3-UNSUBSTITUTED 5-AMINO-4-NITROSOPYRAZOLE COMPOUND, AND 2-HYDROXYIMINO-3-OXOPROPIONITRILE, 3-HYDRAZONO-2-HYDROXYIMINO PROPIONITRILE COMPOUND, AND PROCESSES FOR PRODUCING THESE

This Application is a 371 of PCT/JP03/00647 filed on 24 Jan. 2002, which in turn claims foreign priority under 35 U.S.C. 119 to applications filed in Japan, serial number 2002-15191, filed Jan. 24, 2002, Japan serial number 2002-101259, filed Apr. 03, 2002, Japan serial number 2002-106657, filed Apr. 09, 2002, and Japan serial number 2002-197135, filed Aug. 05, 2002.

TECHNICAL FIELD

The present invention relates to a process for preparing a 3-unsubstituted-5-amino-4-nitrosopyrazole compound which is useful as an intermediate for medicine, agricultural chemicals, etc., and a novel 2-hydroxyimino-3-oxopropionitrile and 3-hydrazono-2-hydroxyiminopropionitrile compound which are used as a synthetic intermediate thereof and processes for preparing the same.

BACKGROUND ART

A 3-unsubstituted-5-amino-4-nitrosopyrazole compound can be utilized as a synthetic intermediate of a 4,5-diaminopyrazole compound which is a useful intermediate for a hair dye or antitumor agent (for example, Japanese Provisional Patent Publications No. 56981/1985, No. 273979/1987 and WO 94/0869).

As a process for preparing a 3-unsubstituted-5-amino-4-nitrosopyrazole compound, in Japanese Provisional Patent Publication No. 273979/1987, etc., there has been disclosed a method of obtaining 5-amino-1-(2-hydroxyethyl)-4-nitrosopyrazole hydrochloride by reacting 5-amino-1-(2-hydroxyethyl)-pyrazole with isoamyl nitrite in the presence of hydrogen chloride. However, in this method, there are problems that the reaction operations are complicated and a yield of the objective material is low.

Also, in J. Chem. Research Synopses, 10 (1992), there is described a method of producing 3-aryl or 3-heterocyclic substituted-4,5-diaminopyrazole compound, but with regard to a 3-position unsubstituted product, a process for preparing an oxime compound which is a starting material thereof is not disclosed, so that it cannot be synthesized. As a prior art with regard to a 3-hydrazono-2-hydroxyiminopropionitrile compound which is used for a process for preparing a 3-unsubstituted-5-amino-4-nitrosopyrazole compound of the present invention, a process for preparing 3-(dimethylhydrazono)-2-hydroxyiminopropionitrile from 3-(β-dimethylhydrazono-α-oxyiminoethyl)-1,2,4-oxadiazole has been described in Khim. Geterotsikl. Soedin., 7, 976 (1991) (English-language translated literature; Chem. Heterocycle Compd., 27 (7), 783 (1991)).

A 3-hydrazono-2-hydroxyiminopropionitrile compound of the present invention is a novel compound, and a process for preparing the same has never been known.

Also, 2-hydroxyimino-3-oxopropionitrile to be used for the process for preparing the 3-unsubstituted-5-amino-4-nitrosopyrazole compound of the present invention is a novel compound, and a process for preparing the same has never been conventionally known.

An object of the present invention is to solve the above-mentioned problems, and to provide a process for preparing a 3-unsubstituted-5-amino-4-nitrosopyrazole compound with a simply and easy method from starting materials which can be easily available with a high yield.

Another object of the present invention is to provide a novel 2-hydroxyimino-3-oxopropionitrile and 3-hydrazono-2-hydroxyiminopropionitrile compound to be used for the preparation of the above-mentioned 3-unsubstituted-5-amino-4-nitrosopyrazole compound and processes for preparing the same.

SUMMARY OF THE INVENTION

A problem of the present invention can be solved by a process for preparing a 3-unsubstituted-5-amino-4-nitrosopyrazole compound represented by the formula (1):

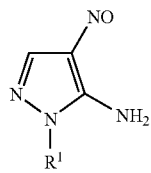

(1)

wherein $R^1$ represents a hydrogen atom, an alkyl group, an aryl group or a heterocyclic group each of which may have a substituent(s), which comprises cyclizing a 3-hydrazono-2-hydroxyiminopropionitrile compound represented by the formula (2):

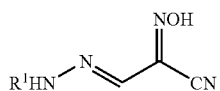

(2)

wherein $R^1$ has the same meaning as defined above.

Also, a problem of the present invention can be solved by a process for preparing a 3-unsubstituted-5-amino-4-nitrosopyrazole compound represented by the formula (1):

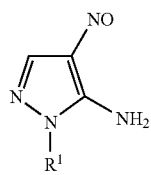

(1)

wherein $R^1$ has the same meaning as defined above, which comprises reacting a nitrosating agent with at least one nitrile compound selected from the group consisting of a 3-alkoxyacrylonitrile represented by the formula (3):

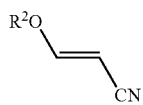

(3)

wherein $R^2$ represents an alkyl group having 1 to 4 carbon atoms, and a 3,3-dialkoxypropionitrile represented by the formula (4):

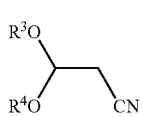

(4)

wherein $R^3$ and $R^4$ may be the same or different from each other, and each represent an alkyl group having 1 to 4 carbon atoms, in the presence of water, to obtain a 2-hydroxyimino-3-oxopropionitrile represented by the formula (5):

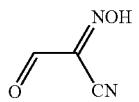

(5)

and then, reacting a hydrazine compound represented by the formula (6):

$R^1HNNH_2$ (6)

wherein $R^1$ has the same meaning as defined above, with the resulting compound.

In the present invention, it is also provided a 3-hydrazono-2-hydroxyiminopropionitrile compound represented by the formula (2):

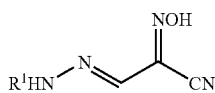

(2)

wherein $R^1$ has the same meaning as defined above.

A process for preparing the 3-hydrazono-2-hydroxyiminopropionitrile compound represented by the above-mentioned formula (2) of the present invention comprises reacting 2-hydroxyimino-3-oxopropionitrile represented by the formula (5):

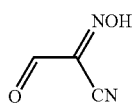

(5)

and a hydrazine compound represented by the formula (6):

$R^1HNNH_2$ (6)

wherein $R^1$ has the same meaning as defined above.

In the present invention, it is further provided 2-hydroxyimino-3-oxopropionitrile represented by the formula (5):

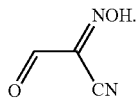

(5)

A process for preparing the 2-hydroxyimino-3-oxopropionitrile represented by the above-mentioned formula (5) of the present invention comprises reacting a nitro-sating agent with at least one of a nitrile compound selected from the group consisting of 3-alkoxyacrylonitrile represented by the formula (3):

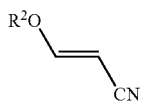

(3)

wherein $R^2$ represents an alkyl group having 1 to 4 carbon atoms, and a 3,3-dialkoxypropionitrile represented by the formula (4):

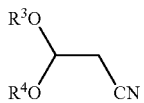

(4)

wherein $R^3$ and $R^4$ may be the same or different from each other, and each represents an alkyl group having 1 to 4 carbon atoms, in the presence of water.

Best Mode for Carrying Out the Invention

The 3-hydrazono-2-hydroxyiminopropionitrile compound to be used in the cyclization reaction in the process for preparing a 3-unsubstituted-5-amino-4-nitrosopyrazole compound represented by the formula (1) of the present invention is a novel compound and represented by the above-mentioned formula (2). In the formula (2), $R^1$ represents a hydrogen atom, or an alkyl group, an aryl group or a heterocyclic group each of which may have a substituent(s). As the above-mentioned alkyl group, there may be mentioned, for example, a methyl group, an ethyl group, a propyl group, a butyl group, a pentyl group, a hexyl group, a heptyl group, etc., as the above-mentioned aryl group, there may be mentioned, for example, a phenyl group, a tolyl group, a xylyl group, etc. As the above-mentioned heterocyclic group, there may be mentioned a pyridyl group, a pyrimidinyl group, a pyridazinyl group, etc. Incidentally, these groups contain various kinds of isomers. Also, as the above-mentioned substituent for the above, there may be mentioned, for example, a hydroxyl group; an alkyl group such as a methyl group, an ethyl group, a propyl group, a butyl group, etc. (these groups contain various kinds of isomers); an alkoxy group such as a methoxy group, an ethoxy group, a propoxy group, a butoxy group, etc. (these groups contain various kinds of isomers); a halogen atom such as a fluorine atom, a chlorine atom, a bromine atom, an iodine atom, etc.; an aryl group such as a phenyl group, a tolyl group, a xylyl group, etc.; a heterocyclic group such as a pyridyl group, a pyrimidinyl group, a pyridazinyl group, etc.; a halogenated alkyl group such as a trifluoromethyl group, etc.; a halogenated alkoxy group such as a difluoromethoxy group, a trifluoromethoxy group, etc.; a nitro group. Also, a position or a number of the substituent(s) are not specifically limited. Incidentally, the compound has an oxime group or a hydrazone group, so that some isomers exist such as an E-isomer or a Z-isomer, etc., and any of the isomers are included in the invention.

The above mentioned $R^1$ is preferably an alkyl group having 1 to 4 carbon atoms (a methyl group, an ethyl group, etc.), an alkyl group having 1 to 4 carbon atoms substituted by a hydroxyl group (a 2-hydroxyethyl group, a 3-hydroxypropyl group, etc.), a phenyl group, a phenyl group substituted by an alkyl group having 1 to 4 carbon atoms (a 4-methylphenyl group, etc.), a phenyl group substituted by a halogen atom (4-chlorophenyl group, etc.), more preferably an alkyl group having 1 to 4 carbon atoms substituted by a hydroxyl group, and above all, a hydroxyethyl group is particularly preferred.

The cyclization reaction of the present invention is preferably carried out in the presence of a solvent. The solvent is not specifically limited so long as it does not inhibit the reaction, and there may be mentioned, for example, water; mineral acids such as hydrochloric acid, sulfuric acid, etc.; alcohols such as methanol, ethanol, n-propyl alcohol, isopropyl alcohol, n-butyl alcohol, isobutyl alcohol, sec-butyl alcohol, t-butyl alcohol, etc.; nitriles such as acetonitrile, propionitrile, etc.; aliphatic hydrocarbons such as hexane, heptane, etc.; halogenated aliphatic hydrocarbons such as methylene chloride, chloroform, carbon tetrachloride, etc.; aromatic hydrocarbons such as benzene, toluene, etc.; halogenated aromatic hydrocarbons such as chlorobenzene, etc.; ethers such as diethyl ether, diisopropyl ether, tetrahydrofuran, dioxane, etc.; carboxylic acids such as acetic acid, propionic acid, etc.; amides such as N,N-dimethylformamide, N,N-dimethylacetamide, etc.; sulfoxides such as dimethylsulfoxide, etc.; carboxylates such as ethyl acetate, butyl acetate, ethyl propionate, etc., preferably water, alcohols, more preferably water, methanol or n-butyl alcohol is used. Incidentally, these solvents may be used singly or in combination of two or more kinds in admixture.

An amount of the above-mentioned solvents to be used can be optionally controlled by a uniformity of the reaction solution or stirrability of the same, and it is preferably 0.5 to 100 g, more preferably 1 to 50 g based on 1 g of the 3-hydrazono-2-hydroxyiminopropionitrile compound.

The reaction of the present invention can be carried out by a method, for example, a 3-hydrazono-2-hydroxyiminopropionitrile compound and a solvent are mixed and reacted under stirring, and the like. A reaction temperature at that time is preferably at −20 to 200° C., more preferably at 20 to 150° C., and a reaction pressure is not specifically limited.

Incidentally, in the reaction of the present invention, a reaction rate can be accelerated by presenting an acid such as hydrochloric acid, etc.

In the above-mentioned reaction, when an acid is used, a salt of the 3-unsubstituted-5-amino-4-nitrosopyrazole compound can be obtained, and it is neutralized by a base (for example, aqueous ammonia) to give a free 3-unsubstituted-5-amino-4-nitrosopyrazole compound.

The 3-unsubstituted-5-amino-4-nitrosopyrazole compound obtained by the reaction of the present invention can be isolated and purified by a conventional method, for example, filtration, extraction, concentration, recrystallization, crystallization, column chromatography, etc. after completion of the reaction.

The 3-hydrazono-2-hydroxyiminopropionitrile compound to be used in the cyclization reaction of the present invention is shown by the above-mentioned formula (2), and is a compound obtained by, for example, as shown in the following reaction scheme (7):

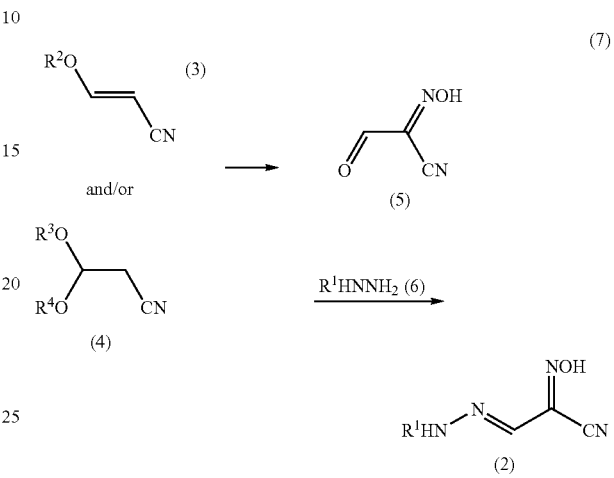

wherein $R^1$ to $R^4$ have the same meaning as defined above, reacting a nitrosating agent with 3-alkoxyacrylonitrile and/or 3,3-dialkoxypropionitrile to obtain 2-hydroxyimino-3-oxopropionitrile, and then, a hydrazine compound is reacted thereto (described in the following Examples 1 to 5). Incidentally, in the formula (2), $R^1$ has the same meaning as defined above.

The hydrazine compound to be used in the preparation method of the 3-hydrazono-2-hydroxyiminopropionitrile compound represented by the formula (2) is shown by the above-mentioned formula (6). In the formula (6), $R^1$ has the same meaning as mentioned above.

An amount of the above-mentioned hydrazine compound to be used is preferably 0.6 to 5.0 mol, more preferably 0.8 to 2.0 mol based on 1 mol of the 2-hydroxyimino-3-oxopropionitrile represented by the formula (5).

The above-mentioned reaction of the present invention is carried out in the presence or absence of a solvent. When a solvent is used, it is not specifically limited so long as it does not inhibit the reaction, and there may be mentioned, for example, water; mineral acids such as hydrochloric acid, sulfuric acid, etc.; alcohols such as methanol, ethanol, n-propyl alcohol, isopropyl alcohol, n-butyl alcohol, isobutyl alcohol, sec-butyl alcohol, t-butyl alcohol, etc.; nitrites such as acetonitrile, propionitrile, etc.; aliphatic hydrocarbons such as hexane, heptane, etc.; halogenated aliphatic hydrocarbons such as methylene chloride, chloroform, carbon tetrachloride, etc.; aromatic hydrocarbons such as benzene, toluene, etc.; halogenated aromatic hydrocarbons such as chlorobenzene, etc.; ethers such as diethyl ether, diisopropyl ether, tetrahydrofuran, dioxane, etc.; carboxylic acids such as acetic acid, propionic acid, etc.; amides such as N,N-dimethylformamide, N,N-dimethylacetamide, etc., preferably water, mineral acids, alcohols, ethers, more preferably water, alcohols, particularly preferably water, or methanol is used. Incidentally, these solvents may be used singly or in combination of two or more kinds in admixture.

An amount of the above-mentioned solvent to be used may optionally adjusted depending on the uniformity of the reaction solution or stirrability thereof, and preferably 0 to 100 g, more preferably 0 to 50 g based on 1 g of the 2-hydroxyimino-3-oxopropionitrile.

The reaction of the present invention can be carried out, for example, by mixing 2-hydroxyimino-3-oxopropionitrile, the hydrazine compound and the solvent, and subjecting to the reaction under stirring, or the like. A reaction temperature at the time is preferably −30 to 100° C., more preferably −15 to 50° C., and a reaction pressure is not specifically limited.

Incidentally, in the reaction of the present invention, a reaction rate can be accelerated by presenting an acid such as hydrochloric acid, sulfuric acid, etc.

The 3-hydrazono-2-hydroxyiminopropionitrile compound obtained by the reaction of the present invention can be isolated and purified by a conventional method, for example, filtration, extraction, concentration, recrystallization, crystallization, column chromatography, etc., after completion of the reaction.

The 2-hydroxyimino-3-oxopropionitrile in the present invention is shown by the above-mentioned formula (5). Incidentally, since the compound has an oxime group, there exist some isomers such as E-isomer or Z-isomer, etc., and any isomers are included in the present invention.

The 2-hydroxyimino-3-oxopropionitrile represented by the formula (5) of the present invention can be obtained by reacting a nitrosating agent with at least one of a nitrile compound selected from the group consisting of a 3-alkoxyacrylonitrile represented by the above-mentioned formula (3) and a 3,3-dialkoxypropionitrile represented by the formula (4).

In the formulae (3) and (4), $R^2$, $R^3$ and $R^4$ may be the same or different from each other, and each represent an alkyl group having 1 to 4 carbon atoms. As such an alkyl group, there may be mentioned, for example, a methyl group, an ethyl group, a propyl group, a butyl group. Incidentally, these groups include various kinds of isomers.

As water to be used in the above-mentioned reaction of the present invention, it may be water by-produced at the time of generating a nitrosating agent in addition to water directly added to the reaction system, and an amount thereof to be used is preferably 0.8 to 500 mol, more preferably 1.0 to 250 mol based on 1 mol of the nitrile compound.

As the nitrosating agent to be used in the above-mentioned reaction of the present invention, there may be mentioned, for example, nitrous acid; nitrosyl halides such as nitrosyl fluoride, nitrosyl chloride, nitrosyl bromide, nitrosyl iodide, etc.; nitrosyl carboxylates such as nitrosyl formate, nitrosyl acetate, etc.; and nitrosyl sulfate, preferably nitrosyl halides, nitrosyl sulfate, more preferably nitrosyl chloride or nitrosyl sulfate is used. Incidentally, as the above-mentioned nitrosyl halides, a commercially available product or a gas separately synthesized may be fed into the reaction system as such, or else, a nitrosyl halide may be directly generated in the reaction system by the method of, for example, ① reacting an alkyl nitrite and a hydrogen halide (or its aqueous solution), ② reacting an alkali metal nitrite and a hydrogen halide (or its aqueous solution), or, ③ reacting a nitrogen oxide and a hydrogen halide (or its aqueous solution) and the like.

An amount of the above-mentioned nitrosating agent to be used is preferably 0.5 to 10 mol, more preferably 0.8 to 5 mol based on 1 mol of the nitrite compound.

The above-mentioned reaction of the present invention is carried out in the presence or absence of a solvent. When a solvent is used, it is not specifically limited so long as it does not inhibit the reaction, and there may be mentioned, for example, water, mineral acids such as hydrochloric acid, sulfuric acid, etc., alcohols such as methanol, ethanol, n-propyl alcohol, isopropyl alcohol, n-butyl alcohol, isobutyl alcohol, sec-butyl alcohol, t-butyl alcohol, etc., nitrites such as acetonitrile, propionitrile, etc., aliphatic hydrocarbons such as hexane, heptane, etc., halogenated aliphatic hydrocarbons such as methylene chloride, chloroform, carbon tetrachloride, etc., aromatic hydrocarbons such as benzene, toluene, etc., halogenated aromatic hydrocarbons such as chlorobenzene, etc., ethers such as diethyl ether, diisopropyl ether, tetrahydrofuran, dioxane, etc., carboxylic acids such as acetic acid, propionic acid, etc., amides such as N,N-dimethylformamide, N,N-dimethylacetamide, etc., sulfoxides such as dimethylsulfoxide, etc., preferably water, mineral acids, alcohols, ethers, more preferably water, hydrochloric acid or diisopropyl ether is used. Incidentally, these solvents may be used alone or in combination of two or more kinds in admixture.

An amount of the above-mentioned solvent to be used is optionally adjusted depending on the uniformity of the reaction solution or stirrability of the same, and it is preferably 0 to 100 g, more preferably 0 to 50 g based on 1 g of the nitrile compound.

The reaction of the present invention can be carried out by a method, for example, in the presence of water, a nitrile compound, a nitrosating agent and a solvent are mixed and reacted under stirring, and the like. A reaction temperature at that time is preferably −70 to 100° C., more preferably −30 to 50° C., and a reaction pressure is not specifically limited.

The 2-hydroxyimino-3-oxopropionitrile obtained by the reaction of the present invention can be isolated and purified by a conventional method such as filtration, extraction, concentration, recrystallization, crystallization, column chromatography, etc after completion of the reaction.

In the present invention, when the above-mentioned reactions are carried out continuously, it may be carried out by a method, for example, a nitrile compound, a nitrosating agent and a solvent is mixed and reacted preferably at −70 to 100° C., more preferably at −30 to 50° C. under stirring, and then, a hydrazine compound is added to the mixture and the resulting mixture is reacted preferably at −30 to 200° C., more preferably at −15 to 150° C. under stirring, and the like. A reaction pressure at that time is not specifically limited.

EXAMPLE

Next, the present invention is more specifically explained by referring to Examples, but the scope of the present invention is not limited by these.

Example 1

Synthesis of 2-hydroxyimino-3-oxopropionitrile

In a flask having an inner volume of 25 ml and equipped with a stirring device, a thermometer, a dropping funnel and a condenser were charged 2.0 g (23 mmol) of 97% by weight 3-methoxyacrylonitrile and 5 ml of diisopropyl ether, and the mixture was cooled up to −10° C. while stirring. Then, while maintaining the reaction solution to 5° C. or lower, 3.5 ml of conc. hydrochloric acid was gradually added to the solution. The reaction solution was again cooled up to −10° C., a mixed solution comprising 2.0 g (36 mmol) of sodium nitrite and 3 ml of water was gradually added dropwise thereto, and the mixture was reacted at the same temperature for 1.5 hours, and further at room temperature for 2 hours. After completion of the reaction, the reaction mixture was extracted with ethyl acetate, the organic layer was separated, washed with brine and dried over anhydrous magnesium sulfate. After filtration, the reaction mixture was concentrated under reduced pressure, and the concentrate was purified by silica gel column chromatography (filler: Micro Sphere Gel D-150-60A, eluent: toluene/ethyl acetate=1/1 (volume ratio)) to obtain 2.3 g of 2-hydroxyimino-3-oxopropionitrile as yellow oily product (isolation yield: 100%). Moreover, it was recrystallized from toluene to obtain 0.79 g of 2-hydroxyimino-3-oxopropionitrile as pale yellowish powder.

Incidentally, 2-hydroxyimino-3-oxopropionitrile is a novel compound having the physical properties shown below.

EI-MS (m/z); 98, 53

CI-MS (m/z); 99 (MH$^+$)

$^1$H-NMR (CDCl$_3$, δ (ppm)); 9.60 (1H, s), 10.64 (1H, s)

IR (KBr method, cm$^{-1}$); 3129, 2993, 2831, 1709, 1457, 1428, 1273, 1076, 768, 745.

Example 2

Synthesis of 2-hydroxyimino-3-oxopropionitrile

In a similar apparatus used in Example 1 were charged 1.0 g (11.7 mmol) of 97% by weight 3-methoxyacrylonitrile and 3.6 g (23.4 mmol) of 44.8% by weight aqueous sodium nitrite solution, and the mixture was cooled to −8° C. while stirring. Then, while maintaining the reaction solution to 1° C. or lower, 4.8 g of conc. hydrochloric acid was gradually added to the mixture, and then, the resulting mixture was reacted at −5 to −1° C. for 1.5 hours, and further at room temperature for 1 hour. After completion of the reaction, the reaction mixture was extracted with diisopropyl ether, the organic layer was separated, washed with a saturated brine, and dried over anhydrous magnesium sulfate. After filtration, the reaction mixture was concentrated under reduced pressure, and when the concentrate was analyzed by $^1$H-NMR (the internal standard method), 2-hydroxyimino-3-oxopropionitrile was formed in an amount of 0.83 g (Reaction yield: 73%).

Example 3

(Synthesis of 2-hydroxyimino-3-oxopropionitrile)

In a similar apparatus used in Example 1 were charged 1.0 g (8.7 mmol) of 94% by weight 3,3-dimethoxypropionitrile and 2.4 g (15.6 mmol) of 44.8% by weight aqueous sodium nitrite solution, and the mixture was cooled to −5° C. while stirring. Then, while maintaining the reaction solution to −1° C. or lower, 3.2 g of conc. hydrochloric acid was gradually added to the mixture, and then, the resulting mixture was reacted at −5 to −1° C. for 1 hour, and further at room temperature for 1.5 hours. After completion of the reaction, the reaction mixture was extracted with ethyl acetate, the organic layer was separated, washed with a saturated brine, and dried over anhydrous magnesium sulfate. After filtration, the reaction mixture was concentrated under reduced pressure, and when the concentrate was analyzed by $^1$H-NMR (the internal standard method), 2-hydroxyimino-3-oxopropionitrile was formed in an amount of 0.61 g (Reaction yield: 76%).

Example 4

Synthesis of 2-hydroxyimino-3-oxopropionitrile

In a flask having an inner volume of 100 ml and equipped with a stirring device, a thermometer, a dropping funnel and a condenser were charged 3.0 g (35 mmol) of 97% by weight 3-methoxyacrylonitrile and 24 ml of water, and after the mixture was cooled to 0° C., 13.0 g (41 mmol) of 40% by weight nitrosyl sulfate-sulfuric acid solution was gradually added to the mixture, and then, the resulting mixture was reacted at the same temperature for 1 hour, and further at room temperature for 18 hours. After completion of the reaction, the reaction mixture was washed with toluene, and then the aqueous layer was separated and extracted with ethyl acetate. Then, the organic layer was washed with a saturated brine, and dried over anhydrous magnesium sulfate. After filtration, the reaction mixture was concentrated under reduced pressure, the concentrate was purified by silica gel column chromatography (Filler: Micro Sphere Gel D-150-60A, Eluent: toluene/ethyl acetate=2/1 (volume ratio)) to give 2.9 g (isolation yield: 82%) of 2-hydroxyimino-3-oxopropionitrile as yellow oily product.

Example 5

Synthesis of 3-(2-hydroxyethyl)hydrazono-2-hydroxyiminopropionitrile

In a similar apparatus used in Example 1 were charged 0.98 g (10 mmol) of 2-hydroxyimino-3-oxopropionitrile synthesized by the same method as in Example 1 and 6 ml of methanol, and the mixture was cooled to 5° C. while stirring. Then, 0.80 g (10 mmol) of 95% by weight 2-hydroxyethylhydrazine was added to the mixture at the same temperature, and reacted at room temperature for 1 hour. After completion of the reaction, the reaction mixture was concentrated under reduced pressure, hexane was added to the concentrate, the resulting mixture was filtered and dried under reduced pressure to give 1.55 g (isolation yield: 99%) of 3-(2-hydroxyethyl)hydrazono-2-hydroxyiminopropionitrile as dark brownish solid.

Incidentally, 3-(2-hydroxyethyl)hydrazono-2-hydroxyiminopropionitrile is a novel compound shown by the following physical properties.

$^1$H-NMR (DMSO-d$_6$, δ (ppm)); 3.17 to 3.62 (4H, m), 4.42 to 5.10 (1H, brs), 7.33 (0.2H, s), 7.53 (0.8H, s), 8.33 (0.8H, t), 8.91 (0.2H, t), 11.20 to 13.10 (1H, br)

Example 6

Synthesis of 5-amino-1-(2-hydroxyethyl)-4-nitrosopyrazole

In a flask having an inner volume of 25 ml and equipped with a stirring device, a thermometer and a reflux condenser were charged 0.94 g (6 mmol) of 3-(2-hydroxyethyl)hydrazono-2-hydroxyiminopropionitrile synthesized by the same method as in Example 5 and 6 ml of n-butyl alcohol, and the mixture was reacted at 110° C. for 3 hours, and further at 5 to 10° C. for 1 hour. After completion of the reaction, the reaction mixture was filtered, and the filtrate was dried under reduced pressure to give 0.61 g (isolation yield: 64%) of 5-amino-1-(2-hydroxyethyl)-4-nitrosopyrazole as reddish orange crystal.

Incidentally, physical properties of the 5-amino-1-(2-hydroxyethyl)-4-nitrosopyrazole are as follows.

Melting point; 170.2 to 171.8° C. (dec.)

EI-MS (m/z); 156, 125

CI-MS (m/z); 157 (MH$^+$)

$^1$H-NMR (DMSO-d$_6$, δ (ppm)); 3.60 to 4.03 (4H, m), 4.75 to 5.03 (1H, br), 7.06 (0.2H, s), 7.76 to 8.29 (2H, br), 8.53 (0.8H, s)

Example 7

Synthesis of 5-amino-1-(2-hydroxyethyl)-4-nitrosopyrazole

In a flask having an inner volume of 2000 ml and equipped with a stirring device, a thermometer, a reflux condenser and a dropping funnel was charged 527 g (5.20 mol) of 36% by weight hydrochloric acid, and then, while maintaining the liquid temperature from 15 to 25° C., a mixed solution comprising 100 g (1.18 mol) of 97.7% by weight 3-methoxyacrylonitrile, 300 g (1.43 mol) of 33% by weight aqueous sodium nitrite solution and 200 ml methanol was gradually added dropwise to the solution, and the resulting mixture was reacted at the same temperature for 30 minutes while stirring.

Then, nitrosyl chloride was removed by blowing nitrogen into the reaction system, and then, while maintaining the reaction solution from 15 to 25° C., 115 g (1.22 mol) of 80.5% by weight 2-hydroxyethylhydrazine and 150 ml of water were gradually added dropwise to the mixture, and the resulting mixture was reacted at 40° C. for 2 hours.

After completion of the reaction, the reaction mixture was cooled to 10° C., 90 ml of water was added to the mixture, then, 257 ml (3.81 mol) of 28% by weight aqueous ammonia was gradually added dropwise to the mixture, and the resulting mixture was stirred at 40° C. for 20 minutes, and at 5° C. for 1 hour. The precipitated crystal was filtered, washed with 140 ml of cold water, and then, dried at 40° C. under reduced pressure to give 111.2 g (isolation yield: 60.4%) of 5-amino-1-(2-hydroxyethyl)-4-nitrosopyrazole as reddish orange crystal.

Incidentally, physical properties of the 5-amino-1-(2-hydroxyethyl)-4-nitrosopyrazole are the same as those obtained in Example 6.

Example 8

Synthesis of 5-amino-1-(2-hydroxyethyl)-4-nitrosopyrazole

In a flask having an inner volume of 100 ml and equipped with a stirring device, a thermometer, a reflux condenser and a dropping funnel were charged 5.0 g (43.5 mmol) of 3,3-dimethoxypropionitrile and 13.3 g (87.0 mmol) of 45% by weight aqueous sodium nitrite solution, and after the liquid temperature was cooled to 0° C., 16 g (158 mmol) of 36% by weight hydrochloric acid was gradually added dropwise to the mixture, and the resulting mixture was reacted at the same temperature for 1 hour, and raising the temperature to 25° C., for further 1 hour while stirring.

Then, nitrosyl chloride was removed by blowing nitrogen into the reaction system, and then, 9.8 ml of methanol was added to the reaction solution and the mixture was cooled to 10° C. Thereafter, 5.3 g (56.1 mmol) of 80.5% by weight 2-hydroxyethylhydrazine was gradually added dropwise to the mixture, and the resulting mixture was reacted at 25° C. for 4 hours and at 40° C. for 2 hours while stirring.

After completion of the reaction, the reaction mixture was cooled to 10° C., and after 7 ml (104 mmol) of 28% by weight aqueous ammonia was gradually added dropwise to the mixture, the reaction mixture was concentrated under reduced pressure to precipitate crystal. The precipitated crystal was filtered, washed with 5 ml of cold water, and then dried at 40° C. under reduced pressure to give 3.2 g (isolation yield: 47.2%) of 5-amino-1-(2-hydroxyethyl)-4-nitrosopyrazole as reddish orange crystal.

Example 9

Synthesis of 5-amino-1-methyl-4-nitrosopyrazole

In a flask having an inner volume of 100 ml and equipped with a stirring device, a thermometer, a reflux condenser and a dropping funnel was charged 25.3 g (250 mmol) of 36% by weight hydrochloric acid, and after the liquid temperature was cooled to 15° C., while maintaining the liquid temperature from 15 to 25° C., a mixed solution comprising 5.0 g (58.8 mmol) of 97.7% by weight 3-methoxyacrylonitrile, 15.0 g (72.5 mmol) of 33% by weight aqueous sodium nitrite solution and 10 ml of methanol was gradually added dropwise to the solution, and the resulting mixture was reacted at the same temperature for 15 minutes.

Then, nitrosyl chloride was removed by blowing nitrogen into the reaction system, and then, 3.3 g (72.5 mmol) of methyl hydrazine was gradually added dropwise to the mixture, and the resulting mixture was reacted at 40° C. for 2 hours.

After completion of the reaction, the reaction mixture was cooled to 10° C., and when 16 ml (237 mmol) of 28% by weight aqueous ammonia was gradually added dropwise to the mixture, then crystal was precipitated. The precipitated crystal was filtered, washed with 7 ml of cold water and dried at 40° C. under reduced pressure to give 3.4 g (isolation yield: 44.8%) of 5-amino-1-methyl-4-nitrosopyrazole as reddish brown crystal.

Physical properties of the 5-amino-1-methyl-4-nitrosopyrazole are as follows.

$^1$H-NMR (DMSO-d$_6$, δ (ppm)); 3.51 (2.4H, s), 3.58 (0.6H, s), 7.02 (0.2H, s), 7.85 to 8.20 (2H, br), 8.51 (0.8H, s)

Example 10

Synthesis of 5-amino-1-(2-hydroxyethyl)-4-nitrosopyrazole

In a flask having an inner volume of 1000 ml and equipped with a stirring device, a thermometer, a reflux condenser and a dropping funnel was charged 270 g (2.66 mol) of 36% by weight hydrochloric acid and the solution was cooled to −15° C., then, a mixed solution comprising a solution of 50.0 g (0.59 mol) of 97.7% by weight 3-methoxyacrylonitrile and 100 ml of methanol with 122 g (0.53 mol) of 30% by weight aqueous sodium nitrite solution was added dropwise to the mixture at −15 to −5° C. from the dropping funnel over 1 hour and 45 minutes. After the mixture was stirred at the same temperature for 1 hour, nitrosyl chloride was removed by blowing nitrogen into the reaction solution, and then, 55.9 g (0.59 mol) of 80.0% by weight 2-hydroxyethylhydrazine and 75 ml of water were slowly added to the mixture so that the temperature of the mixture maintained at 10° C. or lower. The mixture was reacted by heating to 50° C. for 2 hours, then, cooled to 10° C., and 50 ml of water was added to the mixture. When 165 ml (2.72 mol) of 28% by weight aqueous ammonia was gradually added to the mixture to neutralize the same, then crystal was precipitated. Further, the mixture was heated to 40° C. and stirred for 20 minutes, then, cooled to 5° C. and stirred for 1 hour, and precipitated crystal was filtered. The precipitated crystal was washed with 90 ml of cold water and dried at 40° C. under reduced pressure to give 57.5 g (isolation yield: 62.6%) of 5-amino-1-(2-hydroxyethyl)-4-nitrosopyrazole as reddish orange crystal.

Example 11

Synthesis of 5-amino-4-nitroso-1-phenylpyrazole

In a flask having an inner volume of 50 ml and equipped with a stirring device, a thermometer, a reflux condenser and a dropping funnel was charged 13.5 g (133 mmol) of 36% by weight hydrochloric acid and the solution was cooled to −15° C., then, a mixed solution comprising a solution of 2.50 g (29.4 mmol) of 97.7% by weight 3-methoxyacrylonitrile and 5 ml of methanol with 6.15 g (26.5 mmol) of 30% by weight aqueous sodium nitrite solution was added dropwise to the mixture at −15 to −5° C. from the dropping funnel over 45 minutes. After the mixture was stirred at the same temperature for 1 hour, nitrosyl chloride was removed by blowing nitrogen into the reaction solution, and then, 3.24 g (29.4 mmol) of 98% by weight phenylhydrazine, 4 ml of methanol and 4 ml of water were added to the mixture. The resulting mixture was heated to 50° C. and reacted for 1 hour, then, cooled to 10° C., 3 ml of water was added to the mixture and 8 ml (132 mmol) of 28% by weight aqueous ammonia was gradually added to the mixture to neutralize the same. Moreover, the mixture was cooled to 5° C. and stirred for 30 minutes, and the formed crystal was filtered. The obtained crystal was washed with 10 ml of cold water and 3 ml of methanol, and then, dried at 40° C. under reduced pressure to give 3.93 g (isolation yield: 71.0%) of 5-amino-4-nitroso-1-phenylpyrazole as an ocherous solid.

Incidentally, physical properties of the 5-amino-4-nitroso-1-phenylpyrazole are as follows.

EI-MS (m/z); 188, 145, 92

CI-MS (m/z); 189 (MH$^+$)

$^1$H-NMR (DMSO-d$_6$, δ (ppm)); 6.83 to 7.31 (5H, m), 7.69 (0.5H, d), 8.00 (0.5H, d), 11.00 (0.5H, s), 11.29 (0.5H, s), 12.80 to 13.75 (1H, br)

Example 12

Synthesis of 5-amino-1-(4-chlorophenyl)-4-nitrosopyrazole

In a flask having an inner volume of 50 ml and equipped with a stirring device, a thermometer, a reflux condenser and a dropping funnel was charged 13.5 g (133 mmol) of 36% by weight hydrochloric acid and the solution was cooled to −15° C., then, a mixed solution comprising a solution of 2.50 g (29.4 mmol) of 97.7% by weight 3-methoxyacrylonitrile and 5 ml of methanol with 6.15 g (26.5 mmol) of 30% by weight aqueous sodium nitrite solution was added dropwise to the mixture at −15 to −5° C. from the dropping funnel over 1 hour. After the mixture was stirred at the same temperature for 1 hour, nitrosyl chloride was removed by blowing nitrogen into the reaction solution, and then, 5.54 g (29.4 mmol) of 98% by weight 4-chlorophenylhydrazine hydrochloride, 10 ml of methanol and 4 ml of water were added to the mixture. The resulting mixture was heated to 50° C. and reacted for 2 hours, then, cooled to 10° C., 5 ml of water was added to the mixture and 12 ml (198 mmol) of 28% by weight aqueous ammonia was gradually added to the mixture to neutralize the same. Moreover, the mixture was cooled to 5° C. and stirred for 30 minutes, and the formed crystal was filtered. The obtained crystal was washed with 20 ml of cold water and 5 ml of methanol, and dried at 40° C. under reduced pressure to give 4.96 g (isolation yield: 75.8%) of 5-amino-1-(4-chlorophenyl)-4-nitrosopyrazole as a yellow solid.

Incidentally, physical properties of the 5-amino-1-(4-chlorophenyl)-4-nitrosopyrazole are as follows.

EI-MS (m/z); 222, 179, 126

CI-MS (m/z); 223 (MH$^+$)

$^1$H-NMR (DMSO-d$_6$, δ (ppm)); 7.02 to 7.38 (4H, m), 7.70 (0.45H, s), 8.01 (0.55H, d), 11.10 (0.45H, s), 11.38 (0.55H, s), 12.90 to 13.80 (1H, br)

Example 13

Synthesis of 5-amino-1-(4-methylphenyl)-4-nitrosopyrazole

In a flask having an inner volume of 100 ml and equipped with a stirring device, a thermometer, a reflux condenser and a dropping funnel was charged 13.5 g (133 mmol) of 36% by weight hydrochloric acid and the solution was cooled to −15° C., then, a mixed solution comprising a solution of 2.50 g (29.4 mmol) of 97.7% by weight 3-methoxyacrylonitrile and 5 ml of methanol with 6.15 g (26.5 mmol) of 30% by weight aqueous sodium nitrite solution was added dropwise to the mixture at −15 to −5° C. from the dropping funnel over 45 minutes. After the mixture was stirred at the same temperature for 1 hour, nitrosyl chloride was removed by blowing nitrogen into the reaction solution, and then, 4.76 g (29.4 mmol) of 98% by weight 4-methylphenylhydrazine hydrochloride, 50 ml of methanol and 10 ml of water were added to the mixture. The resulting mixture was heated to 50° C. and reacted for 1 hour, then, cooled to 10° C., 5 ml of water was added to the mixture and 12 ml (198 mmol) of 28% by weight aqueous ammonia was gradually added to the mixture to neutralize the same. Moreover, the mixture was cooled to 5° C. and stirred for 30 minutes, and the formed crystal was filtered. The obtained crystal was washed with 30 ml of cold water and 10 ml of methanol, and dried at 40° C. under reduced pressure to give 3.91 g (isolation yield: 65.8%) of 5-amino-1-(4-methylphenyl)-4-nitrosopyrazole as a pale greenish yellow solid.

Incidentally, physical properties of the 5-amino-1-(4-methylphenyl)-4-nitrosopyrazole are as follows.

EI-MS(m/z); 202, 159, 106

CI-MS(m/z); 203(MH$^+$)

$^1$H-NMR (DMSO-$d_6$, δ (ppm)); 2.22 (1.35H, s), 2.24 (1.65H, s), 6.93 to 7.13 (4H, m), 7.66 (0.45H, s), 7.96 (0.55H, d), 10.91 (0.45H, s), 11.22 (0.55H, s), 12.70 to 13.70 (1H, br)

UTILIZABILITY IN INDUSTRY

According to the present invention, a process for preparing an objective. 3-unsubstituted-5-amino-4-nitrosopyrazole compound can be provided with an easy and simple method from an easily available starting material with high yield.

Also, according to the present invention, a novel 3-hydrazono-2-hydroxyiminopropionitrile compound and a process for preparing the same can be provided.

Moreover, according to the present invention, a novel 2-hydroxyimino-3-oxopropionitrile and a process for preparing the same can be provided.

The invention claimed is:

1. 2-Hydroxyimino-3-oxopropionitrile represented by the formula (5):

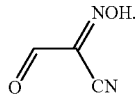

(5)

2. A process for preparing 2-hydroxyimino-3-oxopropionitrile represented by the formula (5):

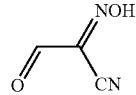

(5)

which comprises reacting a nitrosating agent with at least one nitrile compound selected from the group consisting of a 3-alkoxyacrylonitrile represented by the formula (3):

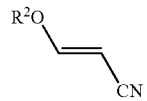

(3)

wherein $R^2$ represents an alkyl group having 1 to 4 carbon atoms,
and a 3,3-dialkoxypropionitrile represented by the formula (4):

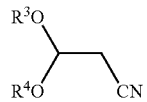

(4)

wherein $R^3$ and $R^4$ may be the same or different from each other and each represent an alkyl group having 1 to 4 carbon atoms,
in the presence of water.

* * * * *